United States Patent [19]

Christensen, IV

[11] Patent Number: 5,602,173

[45] Date of Patent: Feb. 11, 1997

[54] COMPOUNDS USEFUL FOR TREATING ALLERGIC AND INFLAMMATORY DISEASES

[75] Inventor: Siegfried B. Christensen, IV, Philadelphia, Pa.

[73] Assignee: SmithKline Beecham Corporation, Philadelphia, Pa.

[21] Appl. No.: 313,096

[22] PCT Filed: Mar. 5, 1993

[86] PCT No.: PCT/US93/01988

§ 371 Date: Sep. 29, 1994

§ 102(e) Date: Sep. 29, 1994

[87] PCT Pub. No.: WO93/19747

PCT Pub. Date: Oct. 14, 1993

Related U.S. Application Data

[63] Continuation-in-part of Ser. No. 968,760, Oct. 30, 1992, abandoned, which is a continuation-in-part of Ser. No. 862,112, Apr. 2, 1992, abandoned.

[51] Int. Cl.⁶ .................... A61K 31/275; C07C 255/50
[52] U.S. Cl. .................... 514/475; 514/520; 514/521; 514/523; 549/332; 558/426
[58] Field of Search .................... 514/520, 521, 514/523, 475; 549/332; 558/426

[56] References Cited

PUBLICATIONS

Chemical Abstracts, vol. 99 No. 1, Jul. 4, 1983, abstract 99: 5272u.
Chemical Abstracts, vol. 115 No. 1, Jul. 8, 1991, abstract 115: 8542s.
Chemical Abstracts, vol. 90, No. 11, Mar. 12, 1979, abstract 90: 86895p.

*Primary Examiner*—Jacqueline Haley
*Attorney, Agent, or Firm*—James M. Kanagy; Stephen Venetianer; Edward T. Lentz

[57] ABSTRACT

Novel cyclohexane-ylidene derivatives of formula (I) are described. These compounds inhibit the production of Tumor Necrosis Factor and are useful in the treatment of disease states mediated or exacerbated by TNF production. These compounds are also useful in the mediation or inhibition of enzymatic or catalytic activity of phosphodiesterase IV and are therefore useful in the treatment of disease states in need of mediation or inhibition thereof.

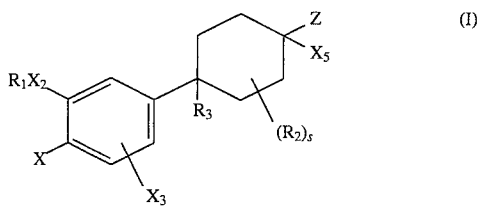

5 Claims, No Drawings

COMPOUNDS USEFUL FOR TREATING ALLERGIC AND INFLAMMATORY DISEASES

This is a National Stage Application of PCT/US93/01988 filed 5 March 1993 and published as WO93/19747 which is a continuation-in-part of U.S. application Ser. No. 07/968,760 filed Oct. 30, 1992, now abandoned; which is a continuation-in-part of U.S. application Ser. No. 07/862,112 filed Apr. 2, 1992, now abandoned.

FIELD OF INVENTION

The present invention relates to novel compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1 ) airway smooth muscle relaxation, 2) inhibition of mast cell mediator release, 3) suppression of neutrophil degranulation, 4) inhibition of basophil degranulation, and 5) inhibition of monocyte and macrophage activation. Hence. compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Antiasthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shook, gram negative sepsis, toxic shook syndrome, adult respiratory. distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for vital replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV profession as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically Candida albicans has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35, (10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of Formula (I), as shown below, useful in the mediation or inhibition of the enzymatic activity (or catalytic activity) of phosphodiesterase IV (PDE IV). The novel compounds of Formula (I) also have Tumor Necrosis Factor (TNF) inhibitory activity.

This invention also relates to the pharmaceutical compositions comprising a compound of Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I), as shown below.

The invention further provides a method for the treatment of allergic and inflammatory disease which comprises administering to a mammal, including humans, in need thereof, an effective amount of a compound of Formula (I).

The invention also provides a method for the treatment of asthma which comprises administering to a mammal, including humans, in need thereof, an effective amount of a compound of Formula (I).

This invention also relates to a method of inhibiting TNF production in a mammal, including humans, which method comprises administering to a mammal in need of such treatment, an effective TNF inhibiting amount of a compound of Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I).

The compounds of Formula (I) are also useful in the treatment of additional viral infections, where such viruses are sensitive to upregulation by TNF or will elicit TNF production in vivo.

The compounds of Formula (I) are also useful in the treatment of yeast and fungal infections, where such yeast and fungi are sensitive to upregulation by TNF or will elicit TNF production in vivo.

The compounds of this invention are represented by Formula (I):

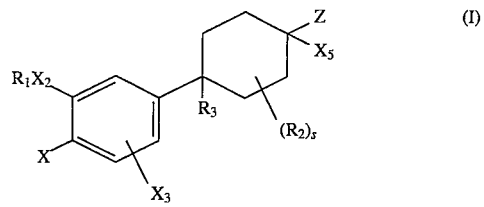

wherein:

$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 1 to 6;

$R_4$ and $R_5$ are independently selected from hydrogen or $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indenyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:

a) when $R_6$ is hydroxyl, then m is 2; or b) when $R_6$ is hydroxyl, then r is 2 to 6; or c) when $R_6$ is 2-tetrahydropyranyl, 2-tetrahydrothiopyranyl, 2-tetrahydrofuranyl, or 2-tetrahydrothienyl, then m is 1 or 2; or d) when $R_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then $R_6$ is other than H in $-(CR_4R_5)_nO(CR_4R_5)_mR_6$;

X is $YR_2$, halogen, nitro, $NR_4R_5$, or formyl amine;

Y is O or $S(O)_{m'}$;

m' is 0, 1, or 2;

X2 is O or $NR_8$;

$X_3$ is hydrogen or X;

$R_2$ is independently selected from $-CH_3$ or $-CH_2CH_3$ optionally substituted by 1 or more halogens;

s is 0 to 4;

$R_3$ is hydrogen, halogen, $C_{1-4}$ alkyl, $CH_2NHC(O)C(O)NH_2$, halo-substituted $C_{1-4}$ alkyl, $-CH=CR_{8'}R_{8'}$, cyclopropyl optionally substituted by $R_{8'}$, CN, $OR_8$, $CH_2OR_8$, $NR_8R_{10}$, $CH_2NR_8R_{10}$, $C(Z')H$, $C(O)OR_8$, $C(O)NR_8R_{10}$, or $C\equiv CR_{8'}$;

Z' is O, $NR_9$, $NOR_8$, NCN, $C(-CN)_2$, $R_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;

Z is $CR_8R_8OR_{14}$, $CR_8R_8OR15$, $CR_8R_8SR_{14}$, $CR_8R_8SR_{15}$, $CR_8R_8S(O)_{m'}R_7$, $CR_8R_8NR_{10}R_{14}$, $CR_8R_8NR_{10}S(O)_2NR_{10}R_{14}$, $CR_8R_8NR_{10}S(O)_2R_7$, $CR_8R_8NR_{10}C(Y')R_{14}$, $CR_8R_8NR_{10}C(O)OR_7$, $CR_8R_8NR_{10}C(Y')NR_{10}R_{14}$, $CR_8R_8NR_{10}C(NCN)NR_{10}R_{14}$, $cR_8R_8NR_{10}C(CR_4NO_2)NR_{10}R_{14}$,
$CR_8R_8NR_{10}C(NCN)SR_9$,
$CR_8R_8NR_{10}C(CR_4NO_2)SR_9$, $CR_8R_8C(O)OR14$,
$CR_8R_8C(Y')NR_{10}R_{14}$, $CR_8R_8C(NR_{10})NR_{10}R_{14}$,
$CR_8R_8CN$, $CR_8R_8$(tetrazolyl), $CR_8R_8$(imidazolyl),
$CR_8R_8$(imidazolidinyl), $CR_8R_8$(pyrazolyl),
$CR_8R_8$(thiazolyl), $CR_8R_8$(thiazolidinyl),
$CR_8R_8$(oxazolyl), $CR_8R_8$(oxazolidinyl),
$CR_8R_8$(triazolyl), $CR_8R_8$(isoxazolyl),
$CR_8R_8$(oxadiazolyl), $CR_8R_8$(thiadiazolyl),
$CR_8R_8$(morpholinyl), $CR_8R_8$(piperidinyl),
$CR_8R_8$(piperazinyl), $CR_8R_8$(pyrrolyl),
$CR_8R_8C(NOR_8)R_{14}$, $CR_8R_8C(NOR_{14})R8$,
$CR_8R_8NR_{10}C(NR_{10})SR_9$, $CR_8R_8NR_{10}C(NR_{10})NR_{10}R_{14}$, $CR_8R_8NR_{10}C(O)C(O)NR_{10}R_{14}$, or $CR_8R_8NR_{10}C(O)C(O)OR_{14}$;

$X_5$ is H, $R_9$, $OR_8$, CN, $C(O)R_8$, $C(O)OR_8$, $C(O)NR_8R_8$, or $NR_8R_8$; or Z and $X_5$ together is —$CR_8R_8O$—;

Y' is O or S;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$cycloalkyl, (2-, 3-or 4-pyridyl), pyrimidyl, pyrazolyl, (1-or 2-imidazolyl) thiazolyl, triazolyl, pyrrolyl, piperazinyl, piperidinyl, morpholinyl, furanyl, (2-or 3-thienyl), (4- or 5-thiazolyl), quinolinyl, naphthyl, or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR10R_{11}$ they may together with the nitrogen form a 5 to 7 membered ting optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms selected from O, N, or S;

$R_{15}$ is $C(O)R_{14}$, $C(O)NR_8R_{14}$, $S(O)_2NR_8R_{14}$, $S(O)_2R_7$;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1;

g) when $X_2R_1$ is $OCF_2H$ or $OCF_3$, X is F, $OCF_2H$ or $OCF_3$, $X_3$ is H, s is zero, $X_5$ is H, Z is $CH_2OR_{14}$, and $R_{14}$ is $C_{1-7}$ unsubstituted alkyl, then $R_3$ is other than H;

or a pharmaceutically acceptable salt thereof.

DETAILED DESCRIPTION OF THE INVENTION

This invention relates to the novel compounds of Formula (I), and to pharmaceutical compositions comprising a compound of Formula (I) and a pharmaceutically acceptable carrier or diluent. This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus, [Kidney Int., 37:362, 1990; Kidney Int., 35:494, 1989] and central nervous system disorders such as depression and multi-infarct dementia.

The compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibitors of Formula (1 ). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I).

The compounds of Formula (I) may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of Formula (I) are also useful in the treatment of yeast and fungal infections, where such yeast and fungi are sensitive to upregulation by TNF or will elicit TNF production in vivo. A preferred disease state for treatment is fungal meningitis. Additionally, the compounds of Formula (I) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The co-administration of the anti-fungal agent with a compound of Formula (I) may be in any preferred composition for that compound such as is well known to those skilled in the art, for instance the various Amphotericin B formulations. Co-administration of an antifungal agent with a compound of Formula (I) may mean simultaneous administration or in practice, separate administration of the agents to the mammal but in a consecutive manner. In particular, the compounds of Formula (I) may be co-administered with a formulation of Amphotericin B, notably for systemic fungal infections. The preferred organism for treatment is the Candida organism. The compounds of Formula (I) may be co-administered in a similar manner with anti-viral or anti-bacterial agents.

The compounds of Formula (I) may also be used for inhibiting and/or reducing the toxicity of an anti-fungal, anti-bacterial or anti-viral agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B.

Preferred compounds are as follows:

When $R_1$ for the compounds of Formula (I) is an alkyl substituted by 1 or more halogens, the halogens are preferably fluorine and chlorine, more preferably a $C_{1-4}$ alkyl substituted by 1 or more fluorines. The preferred halosubstituted alkyl chain length is one or two carbons, and most preferred are the moieties $-CF_3$, $-CH_2F$, $-CHF_2$, $-CF_2CHF_2$, $-CH_2CF_3$, and $-CH_2CHF_2$. Preferred $R_1$ substitutents for the compounds of Formula (I) are $CH_2$-cyclopropyl, $CH_2-C_{5-6}$ cycloalkyl, $C_{4-6}$ cycloalkyl, $C_{7-11}$ polycycloalkyl, (3- or 4-cyclopenteny), phenyl, tetrahydrofuran-3-yl, benzyl or $C_{1-2}$ alkyl optionally substituted by 1 or more fluorines, $-(CH_2)_{1-3}C(O)O(CH_2)_{0-2}CH_3$, $-(CH_2)_{1-3}$ $(CH_2)_{0-2}CH_3$, and $-(CH_2)_{2-4}OH$.

When the $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be $-CH_2CH(-CH_3)-$, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published 5 November 1987, whose disclosure is incorporated herein by reference in its entirety.

Z is preferably $CR_8R_8OR_{14}$, $CR_8R_8OR_{15}$, $CR_8R_8SR_{14}$, $CR_8R_8SR_{15}$, $CR_8R_8$ $S(O)_mR_7$, $CR_8R_8NR_{10}R_{14}$, $CR_8R_8NS(O)_2NR_{10}R_{14}$, $CR_8R_8NS(O)_2R_7$, $CR_8R_8NR_{10}C(O)R_{14}$, $CR_8R_8NR_{10}C(O)OR_7$, $CR_8R_8NR_{10}C(O)NR_{10}R_{14}$, $CR_8R_8NR_{10}C(NCN)NR_{10}R_{14}$, $CR_8R_8NR_{10}C(CR_4NO_2)NR_{10}R_{14}$, $CR_8R_8NR_{10}C(NCN)SR_9$, $CR_8R_8NR_{10}C(CR_4NO_2)SR_9$, $CR_8R_8C(O)OR_{14}$, $CR_8R_8C(O)NR_{10}R_{14}$, $CR_8R_8C(NR_{10})NR_{10}R_{14}$, $CR_8R_8CN$, $CR_8R_8C(NOR_8)R_{14}$, $CR_8R_8C(NOR_{14})R_8$, $CR_8R_8NR_{10}C(NR_{10})SR_9$, $CR_8R_8NR_{10}C(NR_{10})NR_{10}R_{14}$, $CR_8R_8NR_{10}C(O)C(O)NR_{10}R_{14}$, or $CR_8R_8NR_{10}C(O)C(O)OR_{14}$; most preferred are those compounds wherein the $R_8$ group of Z is H and the $R_{14}$ group of Z is $R_4$.

Preferred $X_5$ groups are H, OH, $OCH_3$, CN, $C(O)R_8$, $C(O)OH$, $C(O)OCH_3$, $C(O)NH_2$, $CON(CH_3)_2$, $NH_2$, or $N(CH_3)_2$. The most preferred groups are H, OH, CN, $C(O)OH$, $C(O)NH_2$ or $NH_2$.

The preferred group wherein Z and $X_5$ together is $-CR_8R_8CO-$ is $-CH_2CO-$.

Preferred X groups for Formula (I) are those wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, is a $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a $-CF_3$, $-CHF_2$, or $-CH_2CHF_2$ moiety. Most preferred are the $-CHF_2$ and $-CH_3$ moieties.

Preferred $R_3$ moieties are $C(O)NH_2$, $C\equiv CR_8$, $CH_2NHC(O)C(O)NH_2$, CN, $C(Z')H$, $CH_2OH$, $CH_2F$, $CF_2H$, and $CF_3$. More preferred are $C\equiv CH$ and CN. Z' is preferably O or $NOR_8$.

Preferred $R_7$ moieties include optionally substituted $-(CH_2)_{1-2}$(cyclopropyl), $-(CH_2)_{0-2}$(cyclobutyl), $-(CH_2)_{0-2}$(cyclopentyl), $-(CH_2)_{0-2}$(cyclohexyl), $-(CH_2)_{0-2}$(2-, 3- or 4-pyridyl), $(CH_2)_{1-2}$(2-imidazolyl), $(CH_2)_2$(4-morpholinyl), $(CH_2)_2$(4-piperazinyl), $(CH_2)_{1-2}$(2-thienyl), $(CH_2)_{1-2}$(4-thiazolyl), and $(CH_2)_{0-2}$ phenyl;

Preferred rings when $R_{10}$ and $R_{11}$ in the moiety $-NR_{10}R_{11}$ together with the nitrogen to which they are attached form a 5 to 7 membered ring optionally containing at least one additional heteroatom selected from O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-terazolyl, 1-tetrazolyl, 2-tetrazloyl, morpholinyl, piperazinyl, 4-($R_8$)-1-piperazinyl, or pyrrolyl ring.

Preferred rings when $R_{10}$ and $R_{14}$ in the moiety $-NR_{10}R_{14}$ together with the nitrogen to which they are attached may form a 5 to 7 membered ting optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but are not limited to, 2-($R_7$)-1-imidazolyl, 4-($R_7$)-1-imidazolyl, 5-($R_7$)-1-imidazolyl, 3-(R7)-1-pyrazolyl 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl Applicable nitrogen substitution by R7 includes, but is not limited to, 1-($R_7$)-2-tetrazolyl, 2-($R_7$)-1-tetrazolyl, 4-($R_7$)-1-piperazinyl. Where applicable, the ring may be substituted one or more times by R7.

Preferred groups for $NR_{10}R_{14}$ which contain a heterocyclic ting are 5-($R_{14}$)-1-tetrazolyl, 2-($R_{14}$)-1-imidazolyl, 5-($R_{14}$)-2-tetrazolyl, or 4-($R_{14}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-isoxazolyl),(3-,4- or 5-isoxazolyl), (3-or 5-oxadiazolyl[1,2,4]), (2-oxadiazolyl[1,3,4]), (2-thiadiazolyl [1,3,4]), (2-, 4-, or 5-thiazolyl), (2-, 4-, or 5-oxazolidinyl), (2-, 4-, or 5-thiazolidinyl), or (2, 4-, or 5-imidazolidinyl).

When the $R_7$ group is optionally substituted by a heterocyclic ring such as imidazolyl, pyrazolyl, triazolyl, tetrazolyl, or thiazolyl, the heterocyclic ring itself may be optionally substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazolyl, or 1-($R_8$)-5-triazolyl. Where applicable, the ring may be substituted one or more times by $R_8$.

Preferred are those compounds of Formula (I) wherein $R_1$ is -CH$_2$-cyclopropyl, —CH$_2$—C$_{5-6}$ cycloalkyl, —C$_{4-6}$ cycloalkyl, tetrahydrofuran-3-yl, (3- or 4-cyclopentenyl), benzyl or -C$_{1-2}$ alkyl optionally substituted by 1 or more fluorines, and —(CH$_2$)$_{2-4}$OH; $R_2$ is methyl or fluoro-substituted alkyl, $R_3$ is CN or C≡CR$_8$; and X is YR$_2$.

Most preferred are those compounds wherein $R_1$ is —CH$_2$-cyclopropyl, cyclopentyl, methyl or CF$_2$H; $R_3$ is CN or C≡CH; X is YR$_2$; Y is oxygen; $X_2$ is oxygen; $X_3$ is hydrogen; and $R_2$ is CF$_2$H or methyl.

A preferred subgenus of the compounds of Formula (I) is the compounds of Formula (Ia)

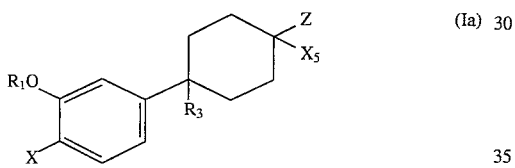

(Ia)

wherein:

$R_1$ is CH$_2$-cyclopropyl, CH$_2$—C$_{5-6}$ cycloalkyl, C$_{4-6}$ cycloalkyl, C$_{7-11}$ polycycloalkyl, (3- or 4-cyclopentenyl), phenyl, tetrahydrofuran-3-yl, benzyl or C$_{1-2}$ alkyl optionally substituted by 1 or more fluorines, —(CH$_2$)$_{1-3}$C(O)O(CH$_2$)$_{0-2}$CH3, —(CH$_2$)$_{1-3}$O(CH$_2$)$_{0-2}$CH3, and —(CH$_2$)$_{2-4}$OH;

X is YR$_2$, halogen, nitro, NR$_4$R$_5$, or formyl amine;

Y is O or S(O)$_{m'}$;

m' is 0, 1, or 2;

$R_2$ is—CH$_3$ or—CH$_2$CH$_3$ optionally substituted by 1 or more halogens;

$R_3$ is hydrogen, C$_{1-4}$ alkyl, CH$_2$NHC(O)C(O)NH$_2$, halo-substituted C$_{1-4}$ alkyl, CN, CH$_2$OR$_8$, C(Z')H, C(O)OR$_8$, C(O)NR$_8$R$_{10}$, or C≡CR$_8$;

Z' is O or NOR$_8$;

Z is CR$_8$R$_8$OR$_{14}$, CR$_8$R$_8$OR$_{15}$, CR$_8$R$_8$SR$_{14}$, CR$_8$R$_8$SR$_{15}$, CR$_8$R$_8$S(O)$_{m'R7}$, CR$_8$R$_8$NR$_{10}$R$_{14}$, CR$_8$R$_8$NS(O)$_2$NR$_{10}$R$_{14}$, CR$_8$R$_8$NS(O)$_2$R$_7$, CR$_8$R$_8$NR$_{10}$C(Y')R$_{14}$, CR$_8$R$_8$NR$_{10}$C(O)OR$_7$, CR$_8$R$_8$NR$_{10}$C(Y')NR$_{10}$R$_{14}$, CR$_8$R$_8$NR$_{10}$C(NCN)NR$_{10}$R$_{14}$, CR$_8$R$_8$NR$_{10}$C(CR$_4$NO$_2$)NR$_{10}$R$_{14}$, CR$_8$R$_8$NR$_{10}$C(NCN)SR$_9$, CR$_8$R$_8$NR$_{10}$C(CR$_4$NO$_2$)SR$_9$, CR$_8$R$_8$C(Y')OR$_{14}$, CR$_8$R$_8$C(Y')NR$_{10}$R$_{14}$, CR$_8$R$_8$C(NR$_{10}$)NR$_{10}$R$_{14}$, CR$_8$R$_8$CN, CR$_8$R$_8$C (NOR$_8$)R$_{14}$, CR$_8$R$_8$C(NOR$_{14}$)R$_8$, CR$_8$R$_8$NR$_{10}$C(NR$_{10}$)SR$_9$, CR$_8$R$_8$NR$_{10}$C(NR$_{10}$)NR$_{10}$R$_{14}$, CR$_8$R$_8$NR$_{10}$C(O)C(O)NR$_{10}$R$_{14}$, or CR$_8$R$_8$NR$_{10}$C(O)C(O)OR$_{14}$;

$X_5$ is H, OR$_8$, CN, C(O)OR$_8$ or NR$_8$R$_8$; or Z and $X_5$ together is —CR$_8$R$_8$CO—;

Y' is O or S;

$R_7$ is —(CR$_4$R$_5$)$_q$R$_{12}$ or C$_{1-6}$ alkyl wherein the R$_{12}$ or C$_{1-6}$ alkyl group is optionally substituted one or more times by methyl or ethyl substituted by 1–3 fluorines, —F, —Br, —Cl, —NO$_2$, —NR$_{10}$R$_{11}$, —C(O)R$_8$, —C(O)OR$_8$, —OR$_8$, —CN, —C(O)NR$_{10}$R$_{11}$, 13 OC(O)NR$_{10}$R$_{11}$, —OC(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$ R$_{11}$, —NR$_{10}$S(O)$_2$R$_9$, —S(O)$_m$R$_9$, —NR$_{10}$C(O)C(O)NR$_{10}$ R$_{11}$, —NR$_{10}$C(O)C(O)R$_{10}$, thiazolyl, imidazolyl, oxazolyl, pyrazolyl, triazolyl, or tetrazolyl;

q is 0, 1, or 2;

$R_{12}$ is C$_3$-C$_7$ cycloalkyl, (2-, 3- or 4-pyridyl), (1- or 2-imidazolyl), piperazinyl, morpholinyl, (2- or 3-thienyl), (4- or 5-thiazolyl), or phenyl;

$R_8$ is independently selected from hydrogen or R$_9$;

$R_9$ is C$_{1-4}$ alkyl optionally substituted by one to three fluorines;

$R_{10}$ is OR$_8$or R$_{11}$;

$R_{11}$ is hydrogen or C$_{1-4}$ alkyl optionally substituted by one to three fluorines; or when R$_{10}$ and R$_{11}$ are as NR$_{10}$R$_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;

$R_{14}$ is hydrogen or R$_7$; or when R$_{10}$ and R$_{14}$ are as NR$_{10}$R$_{14}$ they may together with the nitrogen form a 5 to 7 membered ring optionally containing one or more additional heteroatoms selected from O, N, or S;

$R_{15}$ is C(O)R$_{14}$, C(O)NR$_8$R$_{14}$, S(O)$_2$NR$_8$R$_{14}$, S(O)$_2$R$_7$;

provided that:

a) when $R_{12}$ is N-imidazolyl, N-triazolyl, N-pyrrolyl, N-piperazinyl, or N-morpholinyl, then q is not 1;

b) when $R_1$ is CF$_2$H or CF$_3$, X is F, OCF$_2$H or OCF$_3$, $X_5$ is H, Z is CH$_2$OR$_{14}$, and R$_{14}$ is C$_{1-7}$ unsubstituted alkyl, then $R_3$ is other than H;

or the pharmaceutically acceptable salts thereof.

Preferred compounds of Formula (I) are:

methyl 2-[4-cyano-4-(3-cyclopentyloxy-4-methoxyphenyl)cyclohexan-1-yl]acetate;

cis-[4-cyano-4-(3-cyclopropylmethoxy-4-methoxyphenyl)cyclohexan-1 -yl]methanol;

cis-[4-cyano-4-( 3-cyclopropylmethoxy-4-methoxyphenyl )cyclohexan-1 -yl]methylamine;

cis-[4-cyano-4-( 3-cyclopropylmethoxy-4-methoxyphenyl)cyclohexan-1,1-diyl]oxirane;

cis-[4-cyano-4-(3-cyclopropylmethoxy-4-methoxyphenyl)-1-hydroxycyclohexan-1-yl]methanol;

trans-[4-cyano-4-(3-cyclopropylmethoxy-4-methoxyphenyl)cyclohexan-1,1-diyl]oxirane; and trans-[4-cyano-4-(3-cyclopropylmethoxy-4-methoxyphenyl)-1 -hydroxycyclohexan-1-yl]methanol.

Some of the compounds of Formula (I) may exist in both racemic and optically active forms; some may also exist in distinct diastereomeric forms. All of these compounds are considered to be within the scope of the present invention. Therefore another aspect of the present invention is the administration of either a racemate, a single enantiomeric form, a single diastereomeric form, or mixtures thereof.

DEFINITIONS

The terms "$C_{1-3}$ alkyl", "$C_{1-4}$ alkyl", "$C_{1-6}$ alkyl" or "alkyl" include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like. "Alkenyl" includes both straight or branched chain radicals of 1 to 6 carbon lengths, unless the chain length is limited thereto, including but not limited to vinyl, 1-propenyl, 2-propenyl, 2-propynyl, or 3-methyl-2-propenyl. "Cycloalkyl" or "cycloalkyl alkyl" includes radicals of 3–7 carbon atoms, such as cyclopropyl, cyclopropylmethyl, cyclopentyl, or cyclohexyl. "Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms. "Heteroaryl" means an aromatic ring system containing one or more heteroatoms, such as imidazolyl, triazolyl, oxazolyl, pyridyl, pyrimidyl, pyrazolyl, pyrrolyl, furanyl, or thienyl. "Halo" means chloro, fluoro, bromo, or iodo.

By the phrase "inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

By the term "TNF mediated disease or disease states" is meant any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-60 is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte, but many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines for the present invention include, but are not limited to, Interleukin-1 (IL-1 ), Interleukin-6 (IL-6), Interleukin-8 (IL-8), Tumor Necrosis Factor-alpha (TNF-α) and Tumor Necrosis Factor-beta (TNF-β).

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, his cytokine is TNF-a.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, his cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

METHODS OF PREPARATION

Preparing compounds of Formula (I) can be accomplished by one of skill in the art according to the procedures outlined in the Examples, infra. The preparation of any remaining compounds of Formula (I) not described therein may be prepared by the analogous processes disclosed herein which comprise:

a) for compounds of Formula (I) wherein $R_3$ is other than C(=Z')H and wherein Z is $CH_2COOCH_3$, reacting a compound of Formula (2)

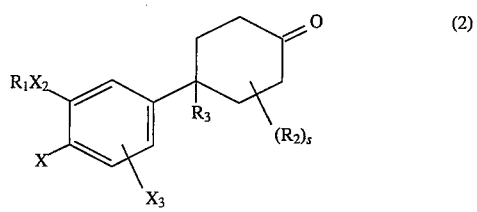

where $R_1$ represents $R_1$ as defined in relation to Formula (I) or a group convertable to $R_1$ and X and $X_3$ represent X and $X_3$ as defined in relation to Formula (I) or a group convertable to X or $X_3$ and $R_3$ represents $R_3$ as defined in relation to Formula (I) or a group convertable to $R_3$, with a stabilized acetate anion, such as sodium trimethylphosphonoacetate or lithium ethyl (trimethylsilyl)acetate, in a suitable non-reacting solvent, such as 1,2-dimethoxyethane or tetrahydrofuran, followed by reduction of the resulting ethylidene intermediate with, e.g., hydrogen and a suitable catalyst, to provide compounds of Formula (I) wherein $R_3$ is other than C(=Z')H and wherein Z is $CH_2COOCH_3$; preparation of such compounds of Formula (I) wherein $R_3$ is C(=Z')H proceed in an analogous fashion from the compound of Formula (2) wherein =Z' is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than O.

Saponification of the ester moiety of compounds of Formula (I) wherein $R_3$ is other than $COOR_8$ and wherein Z is $CH_2COOCH_3$ with, e.g., potassium hydroxide in methanol, provides compounds of Formula (I) wherein $R_3$ is other than $COOR_8$ and wherein Z is $CH_2COOH$; preparation of such compounds of Formula (I) wherein $R_3$ is $COOR_8$ proceed in an analogous fashion from the compound of Formula (2) wherein =Z' is an aldehyde protecting group, such as a dimethylacetal or a dioxolane, followed by deprotection to the aldehyde and subsequent elaboration by standard procedures known to those of skill in the art to the remaining compounds of Formula (I) wherein $R_3$ is $COOR_8$.

Compounds of Formula (I) wherein $R_3$ is other than C(=Z')H and wherein Z is $CH_2OH$ may be prepared in a wide variety of ways. For example, with appropriate manipulation of certain chemically sensitive functional groups, conversion of the ketone of the compounds of Formula (2) wherein $R_1$ represents $R_1$ as defined in relation to Formula (I) or a group convertable to $R_1$ and X and $X_3$ represents X and $X_3$ as defined in relation to Formula (I) or a group convertable to X or $X_3$ and $R_3$ represents $R_3$ as defined in relation to Formula (I) or a group convertable to $R_3$ and wherein $R_3$ is other than C(=Z')H, to the corresponding olefin by Wittig, Peterson or other olefination reactions followed by, e.g., hydroboration-oxidation; preparation of such compounds of Formula (I) wherein $R_3$ is C(=Z')H proceed in an analogous fashion from the compound of Formula (2) wherein =Z' is an aldehyde protecting group, such as a dimethylacetal or a dioxolane, followed by deprotection to the aldehyde and subsequent elaboration by standard procedures known to those of skill in the art to the remaining compounds of Formula (I) wherein Z' is other than O.

Alternatively, compounds of Formula (I) may be obtained by homologation of the ketone of appropriate compounds of Formula (2) by, e.g., ketene thioacetal formation, subsequent hydrolosis to the aldehyde and reduction. Reductive amination with, e.g., ammonium formate and sodium cyanoborohydride in an alcoholic solvent, rather than reduction of such homologated aldehyde intermediates, provides the compounds of Formula (I) wherein $R_3$ is other than C(=Z')H and Z is $CH_2NH_2$; preparation of such compounds of Formula (I) wherein $R_3$ is C(=Z')H proceed in an analogous fashion from the homologated aldehyde intermediates wherein =Z' is an aldehyde protecting group, such as a dimethylacetal or a dioxolane, followed by deprotection to the $R_3$ aldehyde and subsequent elaboration by standard procedures known to those of skill in the art to the remaining compounds of Formula (I) wherein Z' is other than O.

It will be recognized that compounds of Formula (I) may exist in two distinct diastereomeric forms possessing distinct physical and biological properties; such isomers may be separated by standard chromatographic methods. Such isomers may be independently converted to other compounds of Formula (I) wherein Z is, e.g., $CR_8R_8OR_{14}$, $CR_8R_8OR_{15}$, $CR_8R_8NR_{13}R_{14}$, $CR_8R_8NS(O)_2NR_{13}R_{14}$, $CR_8R_8NS(O)_2R_7$, or $CR_8R_8NR_{13}C(Y')R_{14}$, by any of the wide variety of O and N alkylation or acylation procedures known to those of skill in the art.

For example, with proper manipulation of any chemically sensitive functional groups, compounds of Formula (1) wherein $NR_{13}R_{14}$ represent a ring, such as a 1- or 2-tetrazole, may be derived from reaction of an appropriate compound of Formula (I) wherein Z possesses a leaving group, L, as in $CR_8R_8L$, and L is a mesylate, tosylate, chloride or bromide, with the appropriate metal salt of $HNR_{13}R_{14}$, e.g., 5-($R_{14}$)-tetrazole; the appropriate compound of Formula (I) wherein Z is mesylate, tosylate, Br or Cl, derived in turn from the appropriate compound of Formula (1) wherein Z is $CR_8R_8OH$. Using similar procedures but with the appropriate metal salt of $SR_{14}$ or $SR_{15}$, compounds of Formula (I) wherein Z is $CR_8R_8SR_{14}$ or $CR_8R_8SR_{15}$ may be prepared.

Compounds of Formula (2) may be prepared in turn by the processes described in copending application U.S. Ser. No. 07/862,083 filed 2 April 1992.

The following examples are provided to illustrate how to make and use this invention. These examples are not intended to and should not be viewed as limiting the scope or practice of this invention in any way.

SYNTHETIC EXAMPLES

Example 1

4-Cyano-4-(3-Cyclopentyloxy-4-Methoxyphenyl) cyclohexan-1 -one (Intermediate of the Formula 2)

1a. (3-Cyclopentyloxy-4-methoxyphenyl)acetonitrile

To a solution of 3-cyclopentyloxy-4-methoxybenzaldehyde (20 g, 90.8 mmol) in acetonitrile (100 mL) was added lithium bromide (15 g, 173 mmol) followed by the dropwise addition of trimethylsilylchloride (17.4 mL, 137 mmol). After 15 min, the reaction mixture was cooled to 0° C., 1,1,3,3-tetramethyldisiloxane (26.7 mL, 151 mmol) was added dropwise and the resulting mixture was allowed to warm to room temperature. After stirring for 3 h, the mixture was separated into two layers. The lower layer was removed, diluted with methylene chloride and filtered through Celite. The filtrate was concentrated under reduced pressure, dissolved in methylene chloride and refiltered. The solvent was removed in vacuo to provide a light tan oil. To a solution of this crude a-bromo-3-cyclopentyloxy-4-methoxytoluene in dimethylformamide (160 mL) under an argon atmosphere was added sodium cyanide (10.1 g, 206 mmol) and the resulting mixture was stirred at room temperature for 18 h, then poured into cold water (600 mL) and extracted three times with ether. The organic extract was washed three times with water, once with brine and was dried (potassium carbonate). The solvent was removed in vacuo and the residue was purified by flash chromatography, eluting with 10% ethyl acetate/hexanes, to provide an off-white solid (17.7 g, 84%): m.p. 32°–34° C.; an additional quantity (1.3 g) of slightly impure material also was isolated.

1b. Dimethyl 4-cyano-4-(3-cyclopentyloxy-4-methoxyphenyl)pimelate

To a solution of (3-cyclopentyloxy-4-methoxyphenyl)acetonitrile (7 g, 30.3 mmol) in acetonitrile (200 mL) under an argon atmosphere was added a 40% solution of Triton-B in methanol (1.4 mL, 3.03 mmol) and the mixture was heated to reflux. Methyl acrylate (27 mL, 303 mmol) was added carefully, the reaction mixture was maintained at reflux for 5 h and then cooled. The mixture was diluted with ether, was washed once with 1N hydrochloric acid and once with brine, was dried (magnesium sulfate) and the solvent was removed in vacuo. The solid residue was triturated with 5% ethanol/hexane to provide a white solid (9 g, 74%): m.p. 81°–82° C.; and additional 1.1 g (9%) was also obtained from the filtrate. Analysis Calc. for $C_{22}H_{29}NO_6$: C 65.49, H 7.25, N 3.47;found: C 65.47, H 7.11, N 3.49.

1c. 2-Carbomethoxy-4-cyano-4-(3-cyclopentyloxy-4-methoxyphenyl)cyclohexan-1 -one To a solution of dimethyl 4-cyano-4-(3-cyclopentyloxy-4-methoxyphenyl)pimelate (5.9 g, 14.6 mmol) in dry 1,2-dimethoxyethane (120 mL) under an argon atmosphere was added sodium hydride (80% suspension in mineral oil, 1.05 g, 43.8 mmol). The mixture was heated to reflux for 4.5 h, then was cooled to room temperature and was stirred for 16 h. Water was added and the reaction mixture was partitioned between ether and acidic water. The organic extract was dried (magnesium sulfate) and the solvent was removed in vacuo. The residue was purified by flash chromatography, eluting with 3:1 hexanes/ethyl acetate, to provide a white foam (4.9 g, 93%).

Analysis Calc. for $C_{19}H_{23}NO_3 \cdot \frac{1}{4}H_2O$: C67.09, H6.84, N3.72; found: C 66.92, H6.61, N3.74.

1d. 4-Cyano-4-(3-cyclopentyloxy-4-methoxyphenyl)cyclohexan-1-one

A mixture of 2-carbomethoxy-4-cyano-4-(3-cyclopentyloxy-4-methoxyphenyl)cyclohexan-1-one (0.80 g, 2.15 mmol), dimethyl sulfoxide (16 mL), water (1 mL) and sodium chloride (0.8 g) under an argon atmosphere was heated at 140°–145° C. for 5 h. The reaction mixture was cooled and concentrated. The residue was purified by flash chromatography, eluting with 3:1 hexanes/ethyl acetate, to provide a yellow solid. Trituration with hexanes/ethyl acetate yielded a white solid (0.52 g, 77%): m.p. 111°–112° C.

Analysis Calc. for $C_{19}H_{23}NO_3$: C72.82, H7.40, N4.47;found: C72.72, H 7.39, N 4.48.

Example 2

Methyl 2-[4-cyano-4-(3-cyclpropylmethoxy-4-methoxyphenyl)cyclohexan-1-yl]acetate 3a. Methyl 4-cyano-4-(3-cyclpropylmethoxy-4-methoxyphenyl)cyclohexan-1-ylidene acetate A solution of methydiethylphosphonate (1.2 mL, 6.68 mmol) in ethylene glycol dimethyl ether (10 mL) was treated with solid sodium hydride (0.22 g, 7.3 mmol, 80% dispersion in mineral oil) at room temperature under an argon atmosphere. After stirring for 1.5 h, a solution of 4-cyano-4-(3-cyclopropylmethoxy-4-methoxyphenyl)cyclohexanone (1.0 g, 3.34 mmol) was added and the mixture was allowed to stir for an additional 3 h. The reaction mixture was partitioned between methylene chloride and water, was extracted twice, was dried (potassium carbonate) and was evaporated to an oil. Purification by flash column chromatography, eluting with 2:1 hexanes/ethyl acetate, provided an oil (0.48 g, 40%).

Analysis Calc. for $C_{21}H_{25}NO_4 \cdot \frac{1}{8}H_2O$: C70.51, H7.12, N3.92; found: C70.36, H7.01, N3.89.

3b. Methyl 2-[4-cyano-4-(3-cyclpropylmethoxy-4-methoxyphenyl)cyclohexan-1-yl]acetate A solution of methyl 4-cyano-4-(3-cyclpropylmethoxy-4-methoxyphenyl) cyclohexan-1-ylidine acetate (0.19 g, 0.52 mmol) in methanol (10 mL) was hydrogenated with 10% palladium on carbon at 50 psi for 3 h. The reaction mixture was filtered through Celite, was washed with methylene chloride and was evaporated. Purification by flash column chromatography, eluting with 3:1 hexanes/ethyl acetate, provided an oil (0.16 g, 86% ).

Analysis Calc. for $C_{21}H_{27}NO_4$: C70.56, H7.61, N3.92; found: C70.49, H 7.65, N 3.88.

Example 3 cis-[4-Cyano-4-(3-cyclopropylmethoxy-4-methoxyphenyl)cyclohexan-1-yl]methanol

A suspension of methyl 2-[4-cyano-4-(3-cyclopentyloxy-4-methoxyphenyl) cyclohexan-1-yl]acetate (0.18 g, 0.52 mmol) in ether (2.0 mL) with methanol (0.025 mL) and lithium borohydride (0.02 g, 0.78 mmol) was stirred overnight at room temperature under an argon atmosphere. The reaction mixture was partitioned between methylene chloride and acidic water, was extracted three times, was dried (magnesium sulfate) and was evaporated. Purification by flash column chromatography, eluting with 1:1 hexanes/ethyl acetate, provided a white solid (0.1 g, 58.5%): m.p. 119°–120° C. Analysis Calc. for $C_{19}H_{25}NO_3$: C72.35, H7.99, N4.44;found: C71.96, H7.90, N 4.33.

Example 4 cis-[4-Cyano-4-(3-cyclopropylmethoxy-4-methoxypheny)cyclohexan-1-yl]methylamine

A solution of cis-[4-cyano-4-(3-cyclopropylmethoxy-4-methoxyphenyl)cyclohexan-1-yl]methanol (0.05 g, 0.16 mmol) in tetrahydrofuran (1.2 mL) under an argon atmosphere was treated with triphenylphosphine (0.04 g, 0.16 mmol), phthalimide (0.02 g, 0.16 mmol) and then diethylazodicarboxylate (0.03 mL, 0.16 mmol) was added dropwise. The reaction flask was covered with foil and the mixture was stirred at room temperature for 30 h. The solvent was evaporated and the residue was purified by flash column chromatography, eluting with 2:1 hexanes/ethyl acetate, to provide the phthalimide (0.06 g, 89.7%), which was dissolved in ethanol (0.5 mL) under an argon atmosphere and refluxed with hydrazine hydrate (0.08 mL, 0.15 mmol) for 3 h. The reaction was cooled, the precipitate was removed by filtration, the filtrate was applied to a silica column and the product was eluted with 95:5 chloroform/methanol to provide an oil (0.3 g, 60% ).

Analysis Calc. for $C_{19}H_{26}N_2O_3 \cdot \frac{1}{4}H_2O$: C 71.55, H 8.37, N 8.78; found: C 71.47, H 8.21, N 8.67.

Example 5 cis-[4-Cyano-4-(3-cyclopropylmethoxy-4-methoxypheny)cyclohexan-1-yl]methyleneoxide To a mixture of 80% sodium hydride in mineral oil (0.06 g, 2.00 mmol) and trimethylsulfonium iodide (0.41 g, 2.00 mmol) at room temperature under an argon atmosphere was added dropwise dimethylsulfoxide (4 mL) and the reaction mixture was stirred for 0.5 h. A solution of 4-cyano-4-(3-cyclopropylmethoxy-4-methoxyphenyl) cyclohexan-1-one (0.50 g, 1.67 mmol) in dimethylsulfoxide (2 mL) was added and stirring was continued for 45 min. The reaction mixture was quenched with saturated ammonium chloride, was partitioned between ethyl acetate and water, was dried (magnesium sulfate) and the solvent was removed in vacuo. The residue was purified by flash chromatography, eluting with 3:7 ethyl acetate/hexanes, to provide a white solid (0.28 g, 53%): m.p. 90°–91° C.

Analysis Calc. for $C_{19}H_{23}NO_3 \cdot \frac{1}{4}H_2O$: C 71.79, H 7.45, N 4.41; found: C 71.97, H 7.33, N 4.36.

A small amount of the trans-isomer (0.09 g, 17%) was also isolated.

Example 6 cis-[4-Cyano-4-(3-cyclopropylmethoxy-4-methoxypheny)-1-hydroxycyclohexan-1-yl]methanol A mixture of cis-[4-cyano-4-(3-cyclopropylmethoxy-4-methoxyphenyl)cyclohexan-1yl]methyleneoxide (0.14 g, 0.45 retool) and potassium hydroxide (0.02 g, 0.36 mmol) in 85:15 dimethylsulfoxide/water (14 mL) under an argon atmosphere was heated at 100°–110° C. for 1.5 h, was cooled, was diluted with water and was extracted three times with ethyl acetate. The organic extract was washed four times with water, once with brine, was dried (magnesium sulfate) and was evaporated. Purification by flash chromatography, eluting with 2% methanol/dichloromethane, provided the cis-isomer as a white solid (0.09 g, 60%): m.p. 48°–50° C.

Analysis Calc. for $C_{19}H_{25}NO_4 \cdot \frac{1}{8}H_2$: C 68.39, H 7.63, N 4.20; found: C 68.23, H 7.59, N 4.13.

Example 7 trans-[4-Cyano-4-(3-cyclopropylmethoxy-4-methoxyphenyl)-1-cyclohexan-1-yl]methyleneoxide To a mixture of 80% sodium hydride in mineral oil (0.33 g, 11 mmol) and trimethylsulfoxonium iodide (1.69 g, 7.67 mmol) at room temperature under an argon atmosphere was added dropwise dimethylsulfoxide (12 mL) and the reaction mixture was stirred for 30 min. A solution of 4-cyano-4-(3-cyclopropylmethoxy-3-methoxyphenyl)-cyclohexan-1-one (2.00 g, 6.68 mmol) in dimethylsulfoxide (5 mL) was added and stirring was continued for 30 min. The reaction mixture was quenched with saturated ammonium chloride, was partitioned between ethyl acetate and water, was dried (magnesium sulfate) and the solvent was removed in vacuo. The residue was purified by flash chromatography, eluting with 1:3 ethyl acetate/hexanes, to provide a colorless oil (1.42 g, 68%).

Analysis Calc. for $C_{19}H_{23}NO_3 \cdot H_2O$: C 68.86, H 7.30, N 4.23; found: C 69.22, H 7.11, N 4.17. Starting material was also recovered (0.6 g, 30%).

Example 8 trans-[4-Cyano-4-(3-cyclopropylmethoxy-4-methoxyphenyl)-1-hydroxycyclohexan-1-yl]methanol A mixture of trans-[4-cyano-4-(3-cyclopropylmethoxy-4-methoxyphenyl)-cyclohexan-1-yl]methyleneoxide (1.31 g, 4.18 mmol) and potassium hydroxide (0.14 g, 2.5 mmol) in 85:15 dimethylsulfoxide/water (140 mL) under an argon atmosphere was heated at 100°–110° C. for 1 h, was cooled, was diluted with water and was extracted three times with ethyl acetate. The organic extract was washed five times with water, was dried (magnesium sulfate) and was evaporated. Purification by flash chromatography, eluting with 3.5:96.5 methanol/dichloromethane, provided the trans-isomer as a sticky white solid: m.p. 38°–42° C. (0.96 g, 69%).

Analysis Calc. for $C_{19}H_{25}NO_4$: C 68.86, H 7.60, N 4.23; found: C 68.96, H 7.62, N 4.03.

METHODS OF TREATMENT

In order to use a compound of Formula (I) or a pharmaceutically acceptable salt thereof may be used neat though a preferred technique is to present them with a carrier/diluent accordance with standard pharmaceutical practice. Any formulation compatible with the chosen method of delivery and the stability of the compound may be used. One skilled in the art will be able to select and prepare an acceptable formulation in accordance with standard practices in the field of the formulary arts.

The compounds of Formula (I) or may be administered orally (when active by this route), oral, intravenous, intraperitoneal, and intramuscular administration, topically, parenterally, or by inhalation in conventional dosage forms prepared by combining such agent with standard pharmaceutical carriers according to conventional procedures in an amount sufficient to produce the desired therapeutic activity.

The amount of a compound of Formula (I) required for therapeutic effect on topical administration will, of course, vary with the compound chosen, the nature and severity of the condition and the animal undergoing treatment, and is ultimately at the discretion of the physician.

The daily dosage regimen for oral administration is suitably about 0.001 mg/kg to 100 mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

UTILITY EXAMPLES

Example A

Inhibitory effect of compounds of Formula (I) on in vitro TNF production by human monocytes The inhibitory effect of compounds of Formula (I) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I). The protocol used in these models is described in Badger et al., EPO published Application 0 411 754 A2, Feb. 6, 1991, and in Hanna, WO 90/15534, Dec. 27, 1990.

The exemplified compounds herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to μM range for compounds of the workings examples described herein for Formula (I) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 µM) of PDE inhibitors for one minute and 1 µM prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunassay of cyclic AMP and cyclic GMP., Adv. Cyclic Nucleotide Res., 10:1–33, 1979. The compounds of the working examples as described herein for Formula (I) have demonstrated a positive EC$_{50}$s in the µM range in the above assay.

No toxic effects are expected when these compounds are administered in accordance with the present invention.

What is claimed is:

1. A compound of Formula (I):

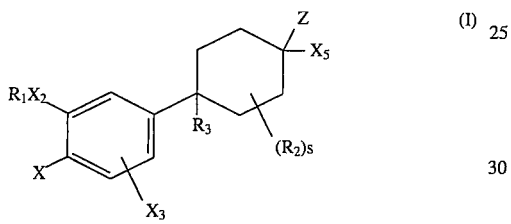

(I)

wherein:

$R_1$ is $-(CR_4R_5)_nC(O)O(CR_4R_5)_mR_6$, $-(CR_4R_5)_nC(O)NR_4(CR_4R_5)_mR_6$,$-(CR_4R_5)_nO(CR_4R_5)_mR_6$, or $-(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxyC$_{1-13}$ alkyl, halo substituted aryloxyC$_{1-13}$ alkyl, indenyl, indenyl, C$_{7-11}$ polycycloalkyl C$_{3-6}$ cycloalkyl, or a C$_{4-6}$ cycloalkyl containing one or two unsaturated bonds, wherein the cycloalkyl moiety may be optionally substituted by 1 to 3 methyl groups or one ethyl group;

provided that:
a) when $R_6$ is hydroxyl, then m is 2; or
b) when $R_6$ is hydroxyl, then r is 2 to 6; or
c) when n is 1 and m is 0, then $R_6$ is other than H in $-(CR_4R_5)_nO(CR_4R_5)_mR_6$;

X is YR$_2$, halogen, nitro, NR$_4$R$_5$, or formyl amine;

Y is O;

m' is a number having a value of 0, 1, or 2;

$X_2$ is O or NR$_8$;

$X_3$ is hydrogen or X;

$R_2$ is independently selected from $-CH_3$ or $-CH_2CH_3$ optionally substituted by 1 or more halogens;

s is 0 to 4;

$R_3$ is CN;

Z is CR$_8$R$_8$OR$_{14}$, CR$_8$R$_8$OR$_{15}$, CR$_8$R$_8$SR14, CR$_8$R$_8$SR$_{15}$, CR$_8$R$_8$S(O)$_{m'}$R$_7$, CR$_8$R$_8$NR$_{10}$R$_{14}$, CR$_8$R$_8$NR$_{10}$S(O)$_2$NR$_{10}$ R$_{14}$, CR$_8$R$_8$NR$_{10}$S(O)$_2$R$_7$, CR$_8$NR$_{10}$C(Y')R$_{14}$, CR$_8$R$_8$NR$_{10}$C(O)OR$_7$, CR$_8$R$_8$NR$_{10}$C(Y')NR$_{10}$R$_{14}$, CR$_8$R$_8$NR$_{10}$C(NCN)NR$_{10}$R$_{14}$, CR$_8$R$_8$NR$_{10}$C(CR$_4$NO$_2$)NR$_{10}$R$_{14}$, CR$_8$R$_8$NR$_{10}$C(NCN)SR$_9$, CR$_8$R$_8$NR$_{10}$C(CR$_4$NO$_2$)SR$_9$, CR$_8$R$_8$C(O)OR$_{14}$, CR$_8$R$_8$C(Y')NR$_{10}$ R$_{14}$, CR$_8$R$_8$C(NR$_{10}$) NR$_{10}$ R$_{14}$, CR$_8$R$_8$CN, CR$_8$R$_8$(tetrazolyl), CR$_8$R$_8$(imidazolyl), CR$_8$R$_8$(imidazolidinyl), CR$_8$R$_8$(pyrazolyl), CR$_8$R$_8$(thiazolyl), CR$_8$R$_8$(thiazolidinyl), CR$_8$R$_8$(oxazolyl), CR$_8$R$_8$(oxazolidinyl), CR$_8$R$_8$(triazolyl), CR$_8$R$_8$(isoxazolyl), CR$_8$R$_8$(oxadiazolyl), CR$_8$R$_8$(thiadiazolyl), CR$_8$R$_8$(morpholinyl), CR$_8$R$_8$(piperidinyl), CR$_8$R$_8$(piperazinyl), CR$_8$R$_8$(pyrrolyl), CR$_8$R$_8$C(NOR$_8$)R$_{14}$, CR$_8$R$_8$C(NOR$_{14}$)R$_8$, CR$_8$R$_8$NR$_{10}$C(NR$_{10}$)SR$_9$, CR$_8$R$_8$NR$_{10}$C(NR$_{10}$)NR$_{10}$ R$_{14}$, CR$_8$R$_8$NR$_{10}$C(O)C(O)NR$_{10}$R$_{14}$, or CR$_8$R$_8$NR$_{10}$C(O)C(O)OR$_{14}$;

Y' is O;

$R_7$ is $-(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, $-F$, $-Br$, $-Cl$, $-NO_2$, $-NR_{10}R_{11}$, $-C(O)R_8$, $-C(O)OR_8$, $-OR_8$, $-CN$, $-C(O)NR_{10}R_{11}$, $-OC(O)NR_{10}R_{11}$, $-OC(O)R_8$, $-NR_{10}C(O)NR_{10}$ R$_{11}$, $-NR_{10}C(O)R_{11}$, $-NR_{10}C(O)OR_9$, $-C(NR_{10})NR_{10}R_{11}$, $-C(NCN)NR_{10}$ R$_{11}$, $-C(NCN)SR_9$, $-NR_{10}C(NCN)SR_9$, $-NR_{10}C(NCN)NR_{10}R_{11}$, $-NR_{10}S(O)_2R_9$, $-S(O)_{m'}R_9$, $-NR_{10}C(O)C(O)NR_{10}R_{11}$, $NR_{10}C(O)C(O)R_{10}$;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is OR$_8$ or R$_{11}$;

$R_{11}$ is hydrogen, or $C_{1-4}$ alkyl optionally substituted by one to three fluorines; or when $R_{10}$ and $R_{11}$ are as NR$_{10}$R$_{11}$ they may together with the nitrogen form a 5 to 7 membered ring optionally containing at least one additional heteroatom selected from O, N, or S;

$R_{14}$ is hydrogen or $R_7$;

$R_{15}$ is C(O)R$_{14}$, C(O)NR$_4$R$_{14}$, S(O)$_2$R$_7$, or S(O)$_2$NR$_4$R$_{14}$;

or the pharmaceutically acceptable salts thereof.

2. A compound of claim 1 wherein $R_1$ is $-CH_2$-cyclopropyl, cyclopentyl, methyl or CF$_2$H;

$R_3$ is CN;

X is YR$_2$;

Y is O;

$X_2$ is oxygen; and $X_3$ is hydrogen.

3. A compound according to claim 2 which is:

methyl 2-[4-cyano-4-(3-cyclopentyloxy-4-methoxyphenyl)cyclohexan-1-yl]acetate;

cis-[4-cyano-4-(3-cyclopropylmethoxy-4-methoxyphenyl)cyclohexan-1-yl]methanol;

cis-[4-cyano-4-(3-cyclopropylmethoxy-4-methoxyphenyl)cyclohexan-1-yl]methylamine;

cis-[4-cyano-4-(3-cyclopropylmethoxy-4-methoxyphenyl)cyclohexan-1,1-diyl]oxirane;

cis-[4-cyano-4-(3-cyclopropylmethoxy-4-methoxyphenyl)-1-hydroxycyclohexan-1-yl]methanol;

trans-[4-cyano-4-(3-cyclopropylmethoxy-4-methoxyphenyl)cyclohexan-1,1-diyl]oxirane; or trans-[4-cyano-4-(3-cyclopropylmethoxy-4-methoxyphenyl)-1-hydroxycyclohexan-1-yl]methanol.

4. A pharmaceutical composition comprising a compound of Formula (I) according to claim 1 and a pharmaceutically acceptable excipient.

5. A method for treating an allergic or inflammatory disease which method comprises administering to a subject in need thereof an effective amount of a compound of Formula (I) according to claim 1 alone or in combination with a pharmaceutically acceptable excipient.

\* \* \* \* \*